United States Patent

Sheinis et al.

Patent Number: 5,289,557
Date of Patent: Feb. 22, 1994

[54] OPTICS FOR MEDICAL LASER

[75] Inventors: Andrew I. Sheinis, Costa Mesa; Colette Cozean, El Toro; John F. Forkner, South Laguna, all of Calif.; M. John Colles, Edinburgh, Scotland

[73] Assignee: Premier Laser Systems, Inc., Irvine, Calif.

[21] Appl. No.: 21,354

[22] Filed: Feb. 23, 1993

Related U.S. Application Data

[62] Division of Ser. No. 644,074, Jan. 18, 1991, Pat. No. 5,198,926.

[51] Int. Cl.$^5$ ............................................. G02B 6/42
[52] U.S. Cl. ..................................... 385/118; 385/119
[58] Field of Search ............... 385/116, 117, 118, 119, 385/92, 93

[56] References Cited

U.S. PATENT DOCUMENTS

| | | | |
|---|---|---|---|
| 3,348,547 | 10/1967 | Kavanagh | 606/4 |
| 3,769,963 | 11/1973 | Goldman et al. | 359/385 |
| 4,228,341 | 10/1980 | Zandberg | 219/121 L |
| 4,342,951 | 8/1982 | Muller et al. | 606/107 |
| 4,362,365 | 12/1982 | Esswein | 359/661 |
| 4,408,602 | 10/1983 | Nakajima | 606/10 |
| 4,471,222 | 9/1984 | Fowler, Jr. et al. | 250/350 |
| 4,491,131 | 1/1985 | Vassiliadis | 128/303.1 |
| 4,494,540 | 1/1985 | Erb | 128/303.1 |
| 4,503,854 | 3/1985 | Jako | 128/303.1 |
| 4,520,816 | 6/1985 | Schachar et al. | 128/303.1 |
| 4,526,447 | 7/1985 | Taylor | 359/196 |
| 4,528,983 | 7/1985 | Erb | 128/303.1 |
| 4,532,400 | 7/1985 | Toida et al. | 219/121 LS |
| 4,545,657 | 10/1985 | Sunago | 359/875 |
| 4,550,240 | 10/1985 | Toida et al. | 219/121 LS |
| 4,565,197 | 1/1986 | Daly | 128/303.1 |
| 4,573,465 | 3/1986 | Sugiyama et al. | 128/303.1 |
| 4,583,539 | 4/1986 | Karlin et al. | 128/303.1 |
| 4,597,380 | 7/1986 | Raif et al. | 128/6 |
| 4,635,632 | 1/1987 | Welber et al. | 128/303.1 |
| 4,638,801 | 1/1987 | Daly et al. | 128/303.1 |
| 4,669,839 | 6/1987 | Muchel | 606/4 |
| 4,679,891 | 7/1987 | Roberts | 359/357 |
| 4,686,992 | 8/1987 | Dewey et al. | 128/303.1 |
| 4,716,399 | 12/1987 | Nordlund | 250/234 |
| 4,917,083 | 4/1990 | Harrington et al. | 606/15 |
| 4,921,318 | 5/1990 | Szumski | 359/356 |
| 4,929,052 | 5/1990 | Colles et al. | 385/147 |
| 4,931,053 | 6/1990 | L'Esperance, Jr. | 606/2 |
| 4,989,962 | 2/1991 | Kebo | 359/354 |
| 4,999,005 | 3/1991 | Cooper | 359/356 |
| 5,074,860 | 12/1991 | Gregory et al. | 606/14 |

FOREIGN PATENT DOCUMENTS

| | | |
|---|---|---|
| 329353 | 2/1989 | European Pat. Off. . |
| 372885 | 12/1989 | European Pat. Off. . |
| 2199960 | 6/1990 | United Kingdom . |

OTHER PUBLICATIONS

Jako, et al., "Carbon Dioxide Laser Microsurgery and its Applications i Laryngology", Department of Otogaryngology, Boston University School of Medicine, Boston, Mass., pp. 330-339.

200A Micromanipulator, Minnesota Laser Corporation, May 1987.

$CO_2$ Laser Micromanipulator for Microscopes and Colposcopes, TTI Medical. (date not available).

Primary Examiner—Frank Gonzalez
Attorney, Agent, or Firm—Knobbe, Martens, Olson & Bear

[57] ABSTRACT

A visible helium neon beam is used as an aiming beam to establish a spot at which a carbon dioxide beam also focuses. The carbon dioxide beam is then employed to vaporize biotic material. A distal end of an articulated arm may couple with the micromanipulator to direct the carbon dioxide beam from the laser through a waveguide and into the micromanipulator. Another aspect of the invention includes introducing the aiming beam into the waveguide through a dichroic mirror positioned in a knuckle joint of the articulated arm. In one embodiment, a laser diode generates the visible light of the aiming beam, and is disposed proximate to the distal end of the articulated arm.

13 Claims, 7 Drawing Sheets

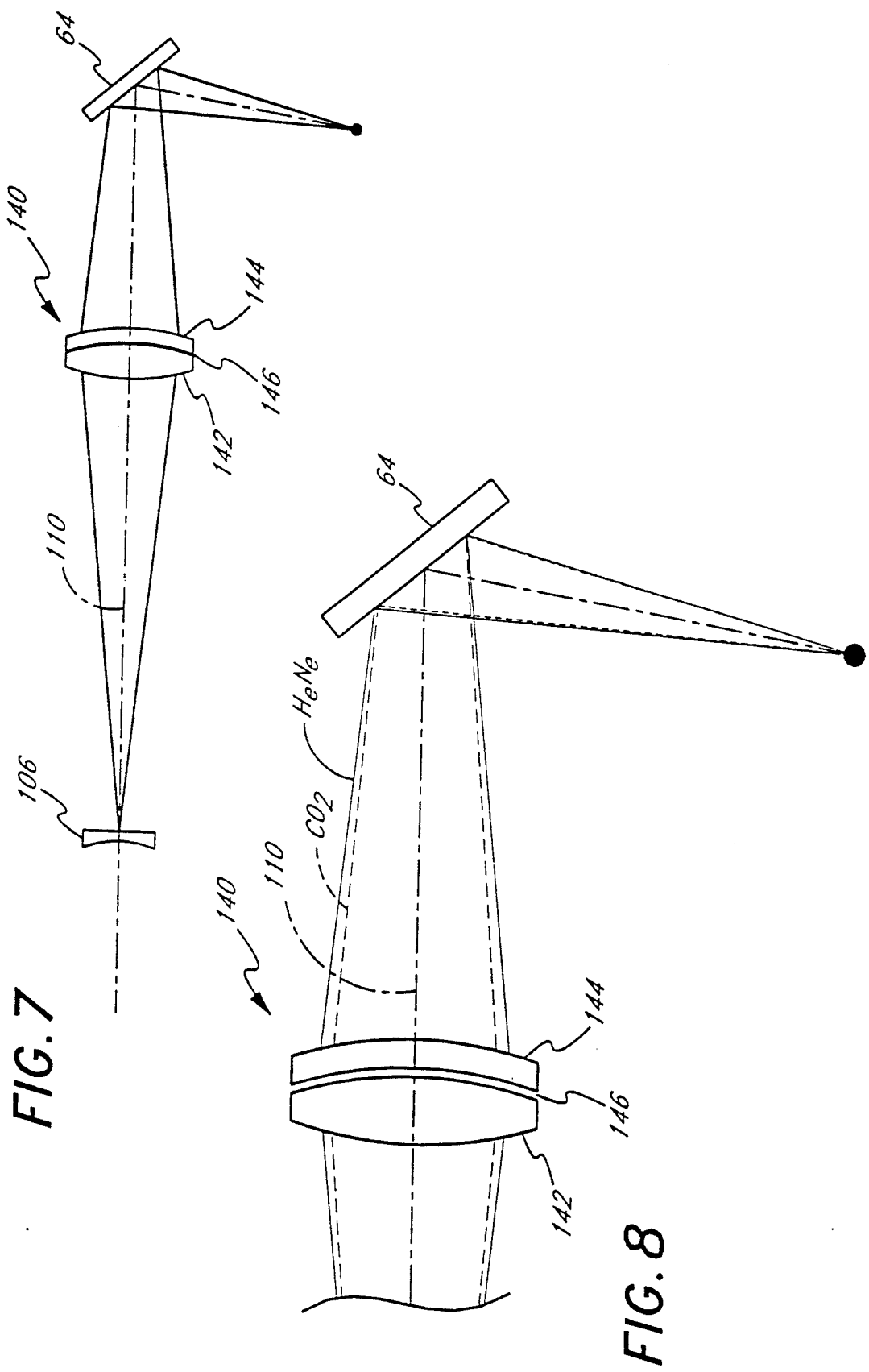

OPTICS FOR MEDICAL LASER

This application is a division of application Ser. No. 07/644,074, filed Jan. 18, 1991 now U.S. Pat. No. 5,198,926.

FIELD OF THE INVENTION

The present invention relates generally to the field of optics and more specifically to the field of laser surgery.

BACKGROUND OF THE INVENTION

Materials such as optical glass can be formed as convergent or divergent lenses. One problem inherent in optical lenses is that when two light beams having significantly different wavelengths pass through a lens material, they will become focused at different points, due to wavelength dispersion. Mathematically, dispersion is defined as the rate of change of the index of refraction (n), with respect to the wavelength ($\lambda$) or $D = dn/d\lambda$. As different wavelengths are transmitted through the lens, the lens exhibits a different index of refraction for each wavelength. Thus, different wavelengths are refracted differently, and thereby focus at different points.

This focusing anomaly for greatly differing wavelengths can be undesirable in certain applications, such as laser surgery. Due to certain desirable properties of laser light outside the visible portion of the spectral range, physicians often perform laser surgery using laser light that is invisible to the human eye, e.g., wavelengths in the far infrared. Because this light cannot be seen by the surgeon, medical laser systems utilizing invisible light typically employ a low power "aiming" laser beam at a visible wavelength. The aiming beam is focused on a patient where an incision is to be made, and then a high power laser beam at an invisible wavelength is applied to make an incision at the point where the low powered beam is focused. Typical medical laser systems employ a helium neon laser, emitting a beam of approximately 0.63 microns wavelength which is not damaging to biotic material, for the low powered aiming beam and a carbon dioxide laser, emitting a beam of approximately 10.6 microns wavelength which vaporizes biotic material, for the high powered cutting beam. The two beams must focus at the same point to ensure the incision is made at the desired location. Even small differences in the location of the focal points of the beams can cause the tissue of a patient to be cut improperly.

Achromatic lens elements are commonly used to align the focal point of two different wavelengths passing through the same optical system. Such elements comprise two different materials which, together, correct for the focusing anomaly caused by dispersion. The different materials of the achromatic lens elements have substantially different indices of refraction and dispersion relationships such that they focus two beams of substantially different wavelengths at the same focal point. However, achromats have typically been used within a moderate range of wavelengths since it is difficult to find two materials which achromatically focus and transmit light over a large wavelength separation. The choices of materials are limited not only by achromatic compatibility, but by absorption properties. Typical optical glasses, for example, do not transmit well at wavelengths approaching 2.7 microns or more due to strong water absorption peaks in the vicinity of three microns. These problems have severely restricted the use of achromats in medical laser systems.

Accordingly, there is a need in the art for an achromatic optical element which will focus widely separated wavelengths, particularly where one of the wavelengths is in the visible portion of the optical spectrum and the other is in the far infrared.

SUMMARY OF THE INVENTION

The present invention comprises an optical system for achromatically focusing light comprised of at least first and second wavelengths such that the light at the first wavelength and the light at the second wavelength are focused substantially at a common location. The optical system comprises an achromatic optical element formed by at least first and second materials, the first and second materials having different dispersions. Both of the first and second materials are transmissive to the first and second wavelengths, the first wavelength being in the visible portion of the optical spectrum and the second wavelength being in the infrared portion of the optical spectrum and being on the order of about two and one-half microns or greater.

In the preferred embodiment, the optical element comprises a first lens and a second lens, the first lens being comprised of the first material and the second lens being comprised of the second material. The first material preferably comprises potassium chloride and the second material preferably comprises zinc selenide. The lenses may be mounted with an air space therebetween and are preferably arranged such that the light passes through the first material before passing through the second material. The first lens may comprise a positive bi-convex lens and the second lens may comprise a negative meniscus lens, thereby forming a positive doublet lens. Additionally the optical system may comprise a second optical element which comprises a negative singlet lens. The negative singlet lens and the positive doublet lens may be arranged substantially in a Galilean telescope configuration, wherein the singlet lens has a principal axis and the doublet lens has a principal axis, the axes being aligned along a propagation path of the light of the first and second wavelengths.

The achromatic optical element is preferably mounted in a micromanipulator. The light of the second wavelength may be of sufficiently high intensity to vaporize biotic material, such as tissue, and may be produced by a carbon dioxide laser having a wavelength of 10.6 microns. The light of the first wavelength may be of sufficiently low intensity that the biotic material is substantially unaffected by the light of the first wavelength, and may be produced by a helium neon laser having a wavelength of 632.8 nanometers.

In accordance with another aspect of the present invention, an achromatic optical element comprises a first lens of potassium chloride and a second lens of zinc selenide. The achromatic optical element preferably consists of a doublet lens, and the first and second lenses may be juxtaposed with an air gap therebetween. A micromanipulator having a housing with an input portion for receiving light and an output portion for outputting light may be utilized to mount the optical element. The lenses are mounted such that light from the input portion passes through the first lens before passing through the second lens. The housing preferably comprises manipulator controls for controlling the direction and focal point of light propagating through the output portion.

The present invention also encompasses a method of focusing an invisible laser light beam having a wavelength of about two and one-half microns or more and a visible aiming light beam. The method comprises passing both the visible and invisible beams through an achromatic optical element such that the visible and invisible beams are focused at a common location.

A method of manufacturing an optical apparatus which is encompassed by the present invention comprises mounting plural lenses to form an achromatic optical element and selecting materials for the lenses which transmit both light having a wavelength in the visible portion of the optical spectrum and light having a wavelength of about three microns or more. In this method, the step of selecting materials preferably comprises the step of selecting potassium chloride for one of the lenses and the step of selecting zinc selenide for another of the lenses.

In accordance with another aspect of the invention, the apparatus for delivery of laser energy for a laser surgery system comprises an articulated arm including a waveguide directing the propagation of laser light and at least one knuckle joint. The knuckle joint has a dichroic mirror to change the direction of the propagating laser light by reflecting substantially all of the laser light. The apparatus further comprises a visible light source, such as a helium neon laser, which emits visible light at about 633 nanometers; or a laser diode which emits visible light having a wavelength of about 670 nanometers. Assembled with the arm, the visible light source is disposed proximate to the distal end of the articulated arm and positioned to introduce visible light into the waveguide through the dichroic mirror at the knuckle joint for the purpose of providing an aiming beam. In the preferred embodiment, the laser light is produced by a carbon dioxide laser and its axis of propagation aligns with the aiming beam axis of propagation when the visible light is introduced into the waveguide.

In accordance with another aspect of the invention, the apparatus for delivery of laser energy for a laser surgery system comprises a laser source emitting laser light, a waveguide linkage directing the laser light along an axis of propagation, a dichromic mirror reflecting the laser light to change the direction of the axis of propagation and a laser diode emitting visible light. A plurality of coupled waveguide segments forms the waveguide linkage. In assembly, the laser diode is disposed proximate to a distal end of the waveguide linkage and is positioned such that visible light passes through the dichroic mirror to couple with the axis of propagation of the laser light. Preferably, the apparatus additionally comprises at least one knuckle joint housing the dichroic mirror.

BRIEF DESCRIPTION OF THE DRAWINGS

FIG. 7 is a schematic view of the optical system of the present invention.

FIG. 8 is an enlarged schematic view of a second end of the optical system of the present invention. Both a visible aiming beam and an invisible laser beam are schematically shown propagating through the optical system.

DETAILED DESCRIPTION OF THE INVENTION

Medical lasers are used in surgery to allow a surgeon to direct a high powered laser beam, capable of vaporizing biotic material, to a precise area on a patient. First, a low power laser beam is aimed at and focused on biotic material, such as tissue. Then, a high power laser beam, which focuses at the same point as the low power aiming beam, is energized to vaporize the biotic material. It is necessary that the two beams focus at the same point so that the incision is made accurately.

Figure 1:
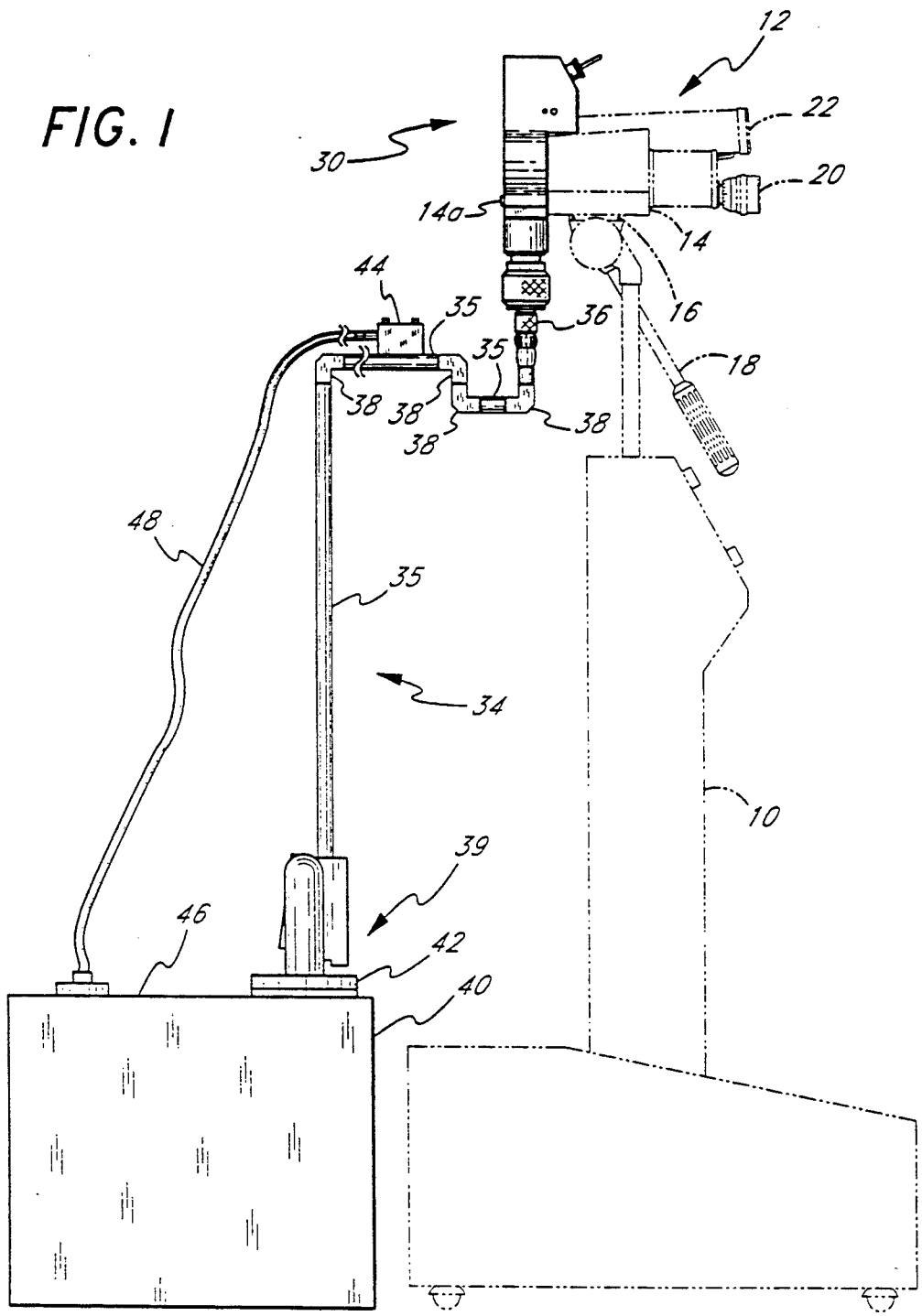
FIG. 1 illustrates a medical laser apparatus having a micromanipulator mounted on a colposcope and stand to be used for gynecological laser surgery and connected to an articulated arm.

FIG. 1 illustrates a micromanipulator system mounted on a stand 10 for use in gynecological surgery. A colposcope 12, or surgical microscope, is mounted on a mounting block 14 which rests atop a rotatable platform 16 at the top of the stand 10. The mounting block 14 has counter sunk holes (not shown) at a forward end 14a. A maneuvering lever 18 extends from just beneath the rotatable platform 16. The colposcope 12 has two adjacent eyepieces 20. An illuminator 22 is located above and between the adjacent eyepieces 20.

A micromanipulator 30, having a housing made of a material such as metal, is supported on the colposcope 12 via a generally bell-shaped orifice 32 (shown in FIG. 4) in the housing. An articulated arm 34 is attached, via a coupling mechanism 94 (shown in FIG. 5), to a lower end of the micromanipulator 30 having a generally cylindrical pilot 31 (shown in FIG. 5) with a hollow center protruding from a collet 36.

As shown in FIG. 1, the articulated arm 34 comprises a linkage of waveguide segments 35 for directing laser light along an axis of propagation 37 (FIG. 3) with a proximal end 39 of the articulated arm 34 connected to a laser source 40 via a quick release connector 42. As used herein, the words proximal and distal are used in reference to proximity of the laser 40 which supplies laser light to the waveguide 35. Preferably, the articulated arm 34 connects to a carbon dioxide laser. The waveguide segments 35 preferably comprise a hollow core ceramic tube.

The articulated arm 34 additionally comprises a plurality of knuckle joints 38 which link the waveguide segments 35 together. Each knuckle joint 38 comprises a set of bearings 41 (FIG. 3) which allows a first waveguide segment to rotate relative to a second waveguide segment. The knuckle joint 38 further comprises a mirror 43 (FIG. 3) which directs light from the second segment into the first segment by reflection and thereby changes the direction of the axis of propagation 37.

The articulated arm 34 further includes a beam combiner 44, shown in FIG. 1, which mounts on the articulated arm 34 near the micromanipulator 30. A low-powered, helium neon laser 46 is coupled into the beam combiner 44 via a fiber-optic waveguide 48, thereby combining the visible helium neon beam and the invisible carbon dioxide beam prior to entry into the micromanipulator 30. Examples of articulated arms are disclosed in U.S. Pat. Nos. 4,917,083 and 4,583,539. The beam combiner 44 may comprise a dichroic mirror mounted in the arm in manner disclosed in U.S. Pat. No. 4,917,083. These patents are incorporated herein by reference.

Figure 2:
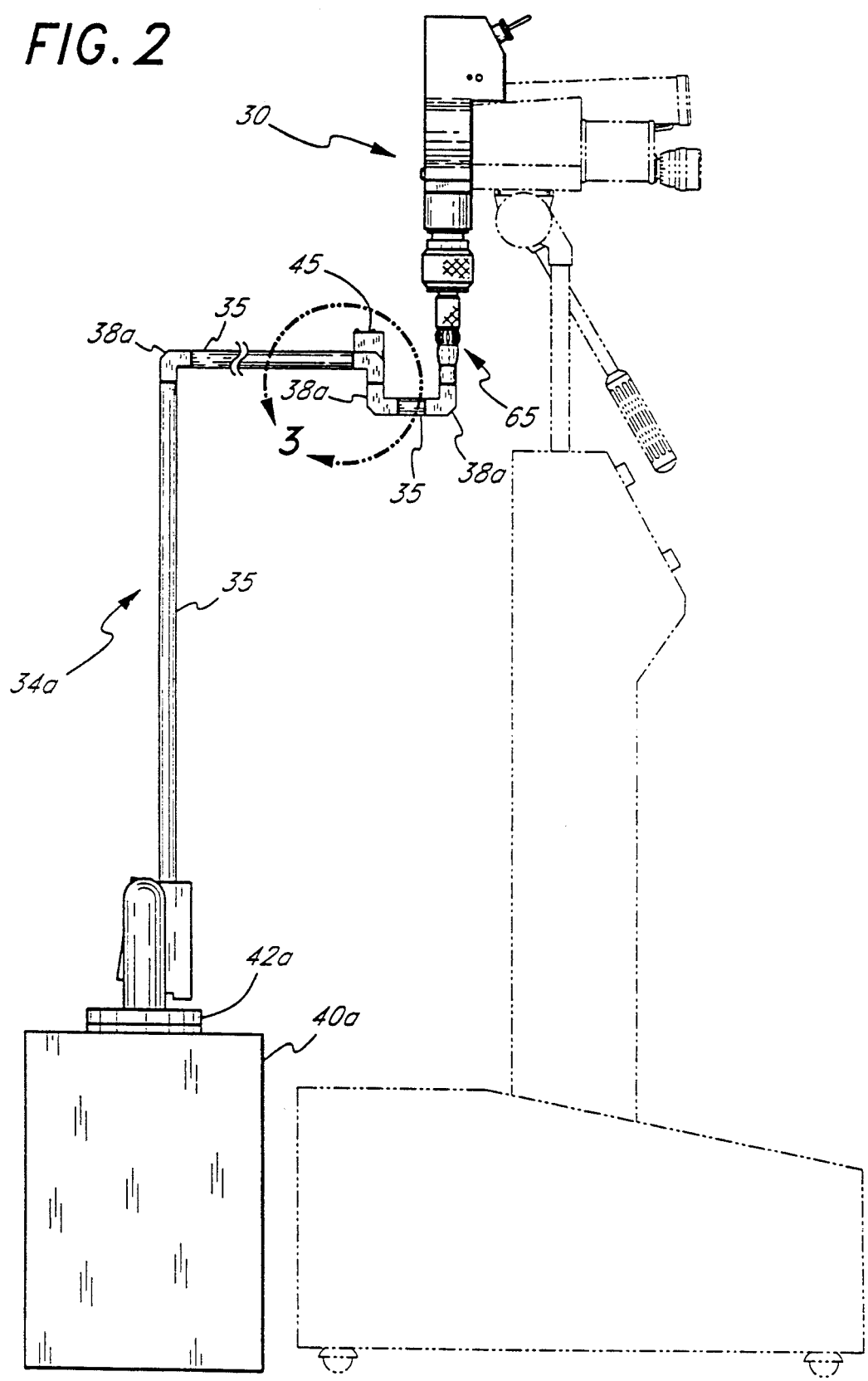
FIG. 2 illustrates an alternative embodiment of the apparatus shown in FIG. 1.
Figure 3:
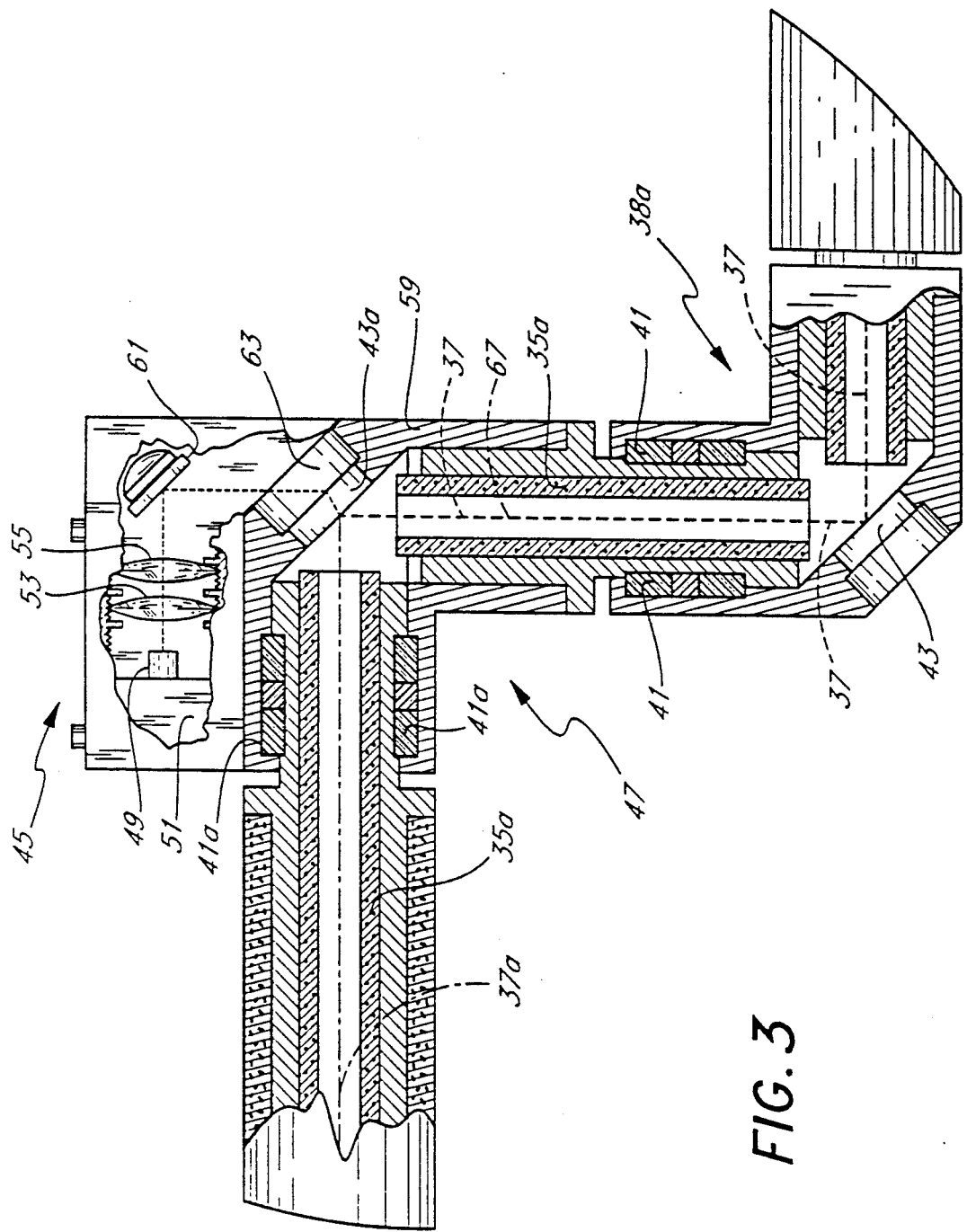
FIG. 3 is an enlarged view of the knuckle joint/beam combiner assembly shown in FIG. 2 relieved to show a laser diode assembly and internal structure of joint/beam combiner.

FIGS. 2 and 3 show an alternative preferred embodiment of the articulated arm 34a. Where appropriate, like numbers with an "a" suffix have been used to indicate like parts between the two embodiments for ease of understanding. The articulated arm 34a comprises a waveguide linkage 35a, a plurality of knuckle joints 38a, and a visible light source 57. One of the knuckle joints comprises a novel a knuckle joint/beam combiner 47, which permits the visible aiming beam to be introduced into the articulated arm through a knuckle joint. The visible light source shown in FIGS. 2 and 3 comprises a laser diode assembly 45. It will be understood, however, that other light sources, such as a helium neon laser, may be used alternatively. However, use of a laser diode reduces costs and produces a more completely integrated articulated arm 34a.

Referring to FIG. 3, the laser diode assembly 45 comprises a laser diode 49 (such as a Toshiba 10 milliwatt laser diode, part no. 1915) which emits visible light having a wavelength on the order of 670 nanometers, a 12 volt power supply 51 (available, e.g., from Power Technology, as part no. 25-4) for powering the laser diode 49, an adjustable collimating lens 53 (such as a Corning molded aspheric lens, part no. 350,150) and an adjustable focusing lens 55 (such as a Corning molded aspheric lens, part no. 350,170). In assembly, the laser diode 49 plugs into the power supply 51 which in turn connects to a 12 volt power supply of a laser source 40a by a pair of electrical leads (not shown). The collimating lens 53 is positioned proximate to the output side of the laser diode 49 and the focusing lens 55 is positioned proximate to the output side of the collimating lens 53. The lenses 53, 55 of the laser diode assembly 45 are adjusted to produce a focused beam of visible light.

The knuckle joint/beam combiner 47 comprises a casing 59 and a set of bearings 41a, housed in the casing 59, which allows a first waveguide segment to rotate relative to a second segment. The joint/combiner 47 further comprises a dichroic mirror 43a, housed in the casing 59, which reflects the carbon dioxide laser beam from the second waveguide segment into the first waveguide segment and transmits the visible light beam. The joint/combiner 47 additionally comprises a mirror 61 which reflects the visible light beam emitted by the laser diode 49 through an aperture 63 in the joint/combiner 47 and onto the dichroic mirror 43a.

In assembly, the joint/combiner 47 is disposed proximate to a distal end 65 of the articulated arm 34a. The laser diode assembly 45 in turn bolts to the joint/combiner 47 and is positioned such that the visible light beam strikes the reflective mirror 61 of the joint/combiner 47.

Introducing the aiming beam at the distal end of the waveguide alleviates alignment problems between the aiming beam and the laser light. Such alignment problems typically occur because of flexure in the waveguide segments. Because the wavelength of the visible light is too short to be guided by the waveguide, the visible aiming beam propagates through the articulated arm by free space transmission. Thus, if any flexure occurs in the waveguide segments, the aiming beam is susceptible to becoming misaligned with the laser light. By introducing the aiming beam at the distal end of the articulated arm, the aiming beam has less distance to travel before it reaches an output end of the articulated arm, and thus, misalignment errors do not have an opportunity to accumulate. Further, by eliminating flexure as a source of alignment errors, more flexure in the waveguide can be tolerated, and thus, the arm can be structured of lighter less expensive material.

In the power up state, the laser light emitted from a segments 35a. This carbon dioxide laser beam reflects off the dichroic mirror 43a of the knuckle joint/beam combiner 47 thereby changing its direction of propagation. The laser diode emits a divergent cone of visible light which passes through the collimating lens 53 and the focusing lens 55 and strikes the surface of the reflective mirror 61. Prior to striking the reflective mirror 61, the visible light beam propagates along an axis which is substantially parallel to the waveguide segment 35a.

The visible light beam reflects off the mirror 61 in a direction passing through the joint aperture 63 and striking the dichroic mirror 43a. The visible light transmits through the dichroic mirror 43a and into the waveguide 35a. the visible light transmits through the dichroic mirror 43a, an axis of propagation 67 of the visible light aiming beam aligns with the axis of propagation 37a of the laser light. In this manner, the visible light is coupled into the waveguide for propagation along the axis of propagation 37a of the carbon dioxide beam. As a result of replacing mirror 43 of the normal knuckle joint 38 with the dichroic mirror 43a, a mirror is eliminated from the articulated arm 34 thereby simplifying the assembly and reducing cost.

Figure 4:
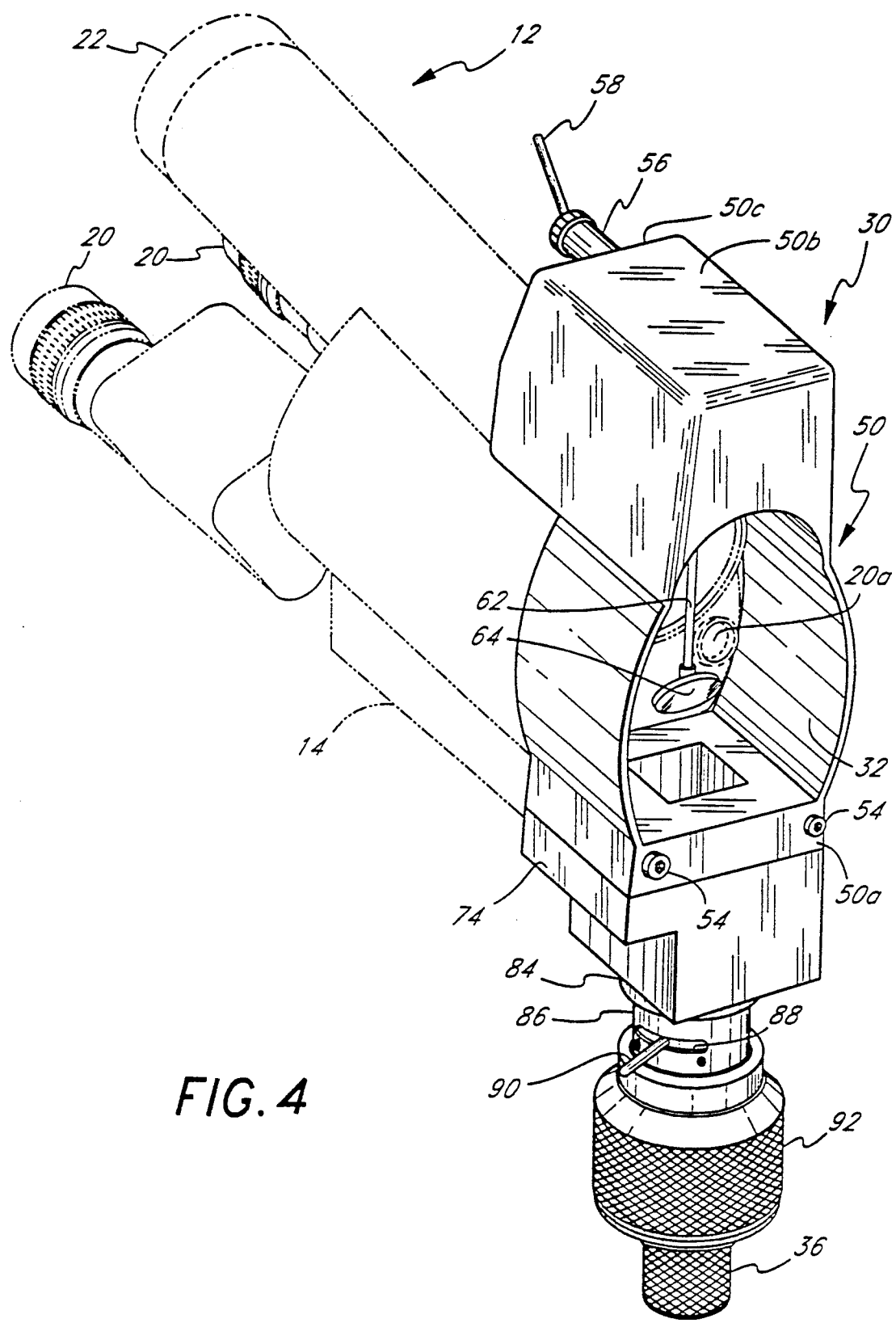
FIG. 4 is an enlarged view of the micromanipulator mounted on the colposcope.
Figure 5:
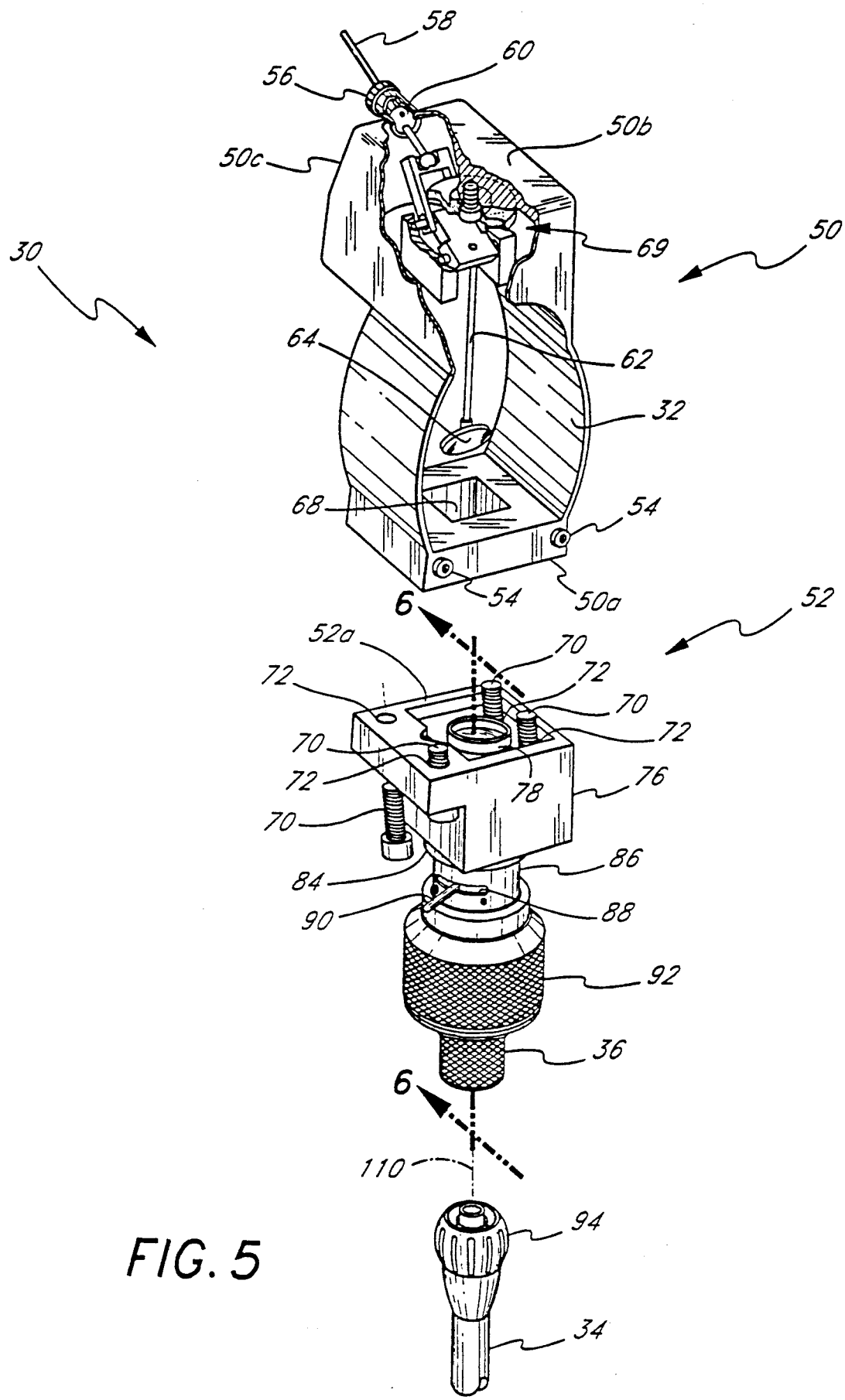
FIG. 5 is an exploded view of the micromanipulator.

Referring to FIGS. 4 and 5, a perspective view of the micromanipulator 30, as mounted on the colposcope 12, and an exploded view of the micromanipulator 30, respectively, are shown. The micromanipulator housing is separable into two parts, a mounting segment 50 and an optical housing 52. When the mounting segment 50 and optical housing 52 are assembled, as in FIG. 4, the optical housing 52 is aligned at a slight angle from the mounting segment 50. Two blind threaded holes (not shown) are located at a first end 50a of the mounting segment. These blind holes align with the counter sunk holes (not shown) located at the forward edge of the mounting block 14. Two screws 54 extend through the apertures and the orifices and secure the micromanipulator 30 to the mounting block 14.

A generally cylindrical ball housing 56, located just below a second end 50b of the mounting segment 50, protrudes from a rear wall 50c of the mounting segment 50. A control toggle 58 protrudes from the ball housing 56. The toggle 58 is connected via a ball joint 60 to a set 69 of levers and ball joints (shown in FIG. 5) that terminate in a cantilevered mirror arm 62 which extends in the orifice 32 between forward ends 20a of the two eyepieces 20 when the micromanipulator 30 is mounted on the colposcope 12. A mirror 64 is affixed at an angle to the end of the mirror arm 62. The mirror 64 rests above a generally square aperture 68 in the first end 50a of the mounting segment 50.

An upper wall 52a of the optical housing 52 is affixed to the first end 50a of the mounting segment 50 via four screws 70 which are threadedly inserted into four counter bored holes 72 (shown in FIG. 5) in the optical housing 52. These counter bored holes 72 are aligned with four threaded holes (not shown) in the first end 50a of the mounting segment 50. Two of the counter bored holes 72 in the upper wall 52a of the optical housing 52 are located on a shoulder 74 protruding from a generally cubic section 76 of the optical housing. A lens retainer ring 78, holding a slightly recessed lens 140, extends from the center of a generally rectangular recess 82 located in the first end 52a of the optical housing. The lens retainer ring 78 is ingressive upon the generally square aperture 68 in the lower wall 50a of the mounting segment 50 when the mounting segment 50 and the optical housing 52 are assembled.

A generally cylindrical housing 84, from which protrudes a second generally cylindrical housing 86 having a slightly smaller diameter, extends from the generally cubic section 76 of the optical housing 52. There is a slot 88 located on a first side 52c of the second cylindrical housing 86. A lever 90 protrudes from the slot 88 and is movable along the axis of the slot 88. A generally cylindrical knurled sleeve 92 is mounted coaxially on the second cylindrical housing 86. The sleeve 92 is rotatable about a central axis. The collet 36, having a smaller diameter than the second cylindrical housing 86, is attached to a lower end of the second cylindrical housing 86 and protrudes from the knurled sleeve 92. The collet 36 connects with the pilot 31 which, in turn, connects with the end of the articulated arm 34 having the coupling mechanism 94 (as shown in FIG. 5).

Figure 6:
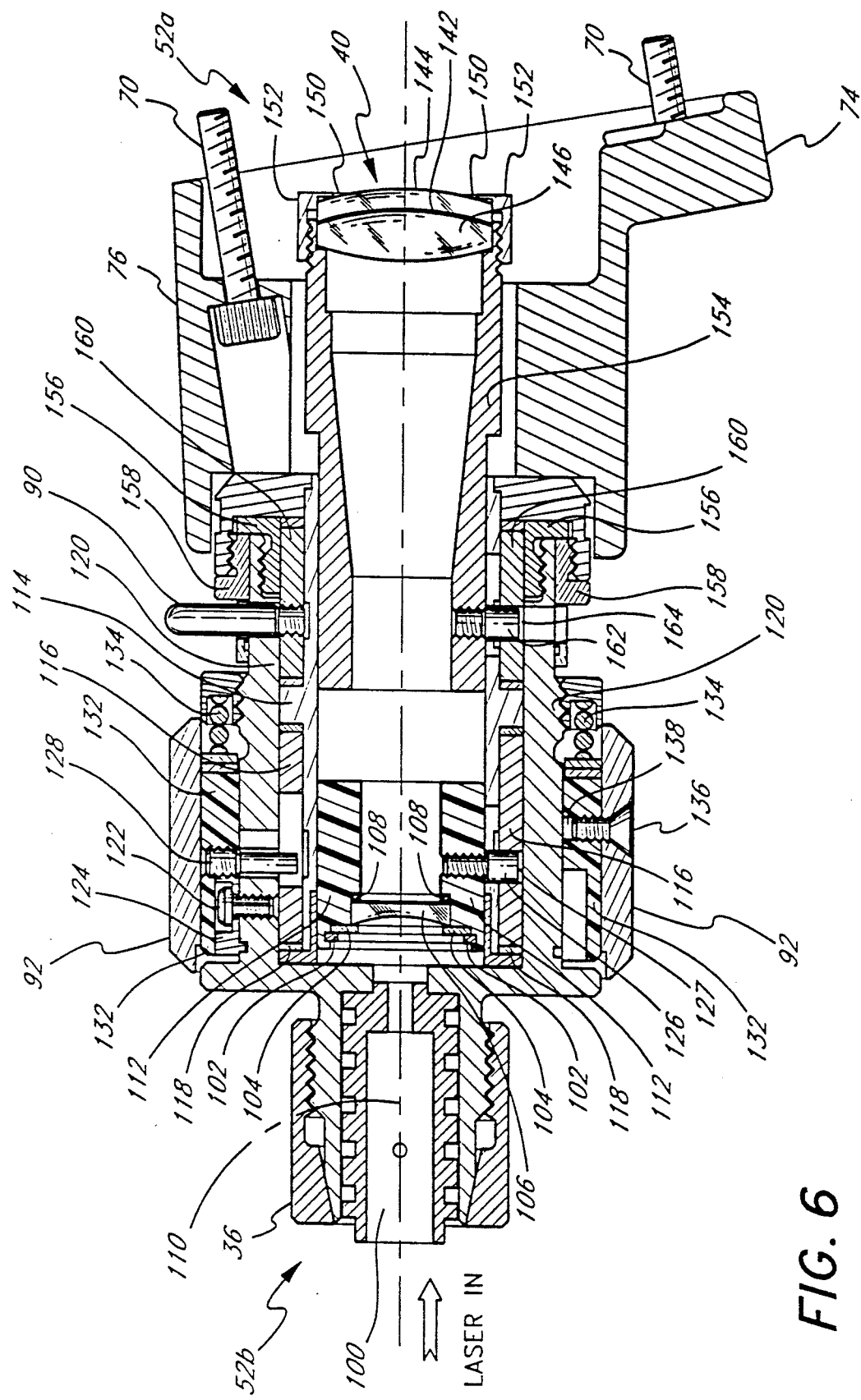
FIG. 6 shows a cross-sectional view of the optical housing of the micromanipulator, taken along line 6—6 in FIG. 5.

Referring to FIG. 6, a cross section, along line 6—6 in FIG. 5, of the optical housing 52 of the micromanipulator 30 is shown. The pilot 31 and collet 36 have a relatively large passage 100 that leads to the interior of a second end 52b of the optical housing, through a snap ring 102 and a lens retainer 104. A negative singlet lens 106, preferably made of zinc selenide, is held by the lens retainer 104 on one side and an O-ring 108 on the other side. A central axis of the passage 100 and the center of the negative lens 106 define an optical axis 110.

The lens retainer 104 is supported by a lens carrier 112. The lens carrier 112 is encased by a lens carrier housing 114 in which a helical slide 116 is embedded. A helical slide retainer 118 is located adjacent the helical slide 116, near the second end 52b of the optical housing 52. Sidewalls 120 of the optical housing 52 encase the lens carrier housing 114. Three clamping screws 122 (only one is shown), located on the first side 52c of the optical housing, are threadedly inserted into a portion of the sidewalls 120 of the optical housing 52. A head of each clamping screw 122 is located within a recess in one of three position stops 124 (only one is shown). The three position stops 124 and clamping screws 122 are aligned along a circumference of a circle in a plane perpendicular to the optical axis 110. A drive pin 126 is threadedly inserted into the lens carrier 112 on a second side 52d of the optical housing 52 which is opposite the first side 52c. A head of the drive pin 126 rests in a helical slot 127 cut into the surface of the helical slide 116.

One end of a focusing lever 128, located on the first side of the optical housing 52, rests within a long, narrow slot 130 arranged parallel to the optical axis 110. An opposite end of the focusing lever 128 is threadedly inserted into a drive ring 132. The drive ring 132 is under tension of a spring 134. The cylindrical knurled sleeve 92 encases the drive ring 132. A connector 136, e.g., a flat head screw, located on the second side 52d of the optical housing 52, threadedly couples the drive ring 132 and the knurled sleeve 92 via a tapped hole 138 in the drive ring 132.

Spaced from the first negative lens 106 along the optical axis 110 is a second optical element comprising a doublet lens 140. The doublet 140 preferably comprises a positive bi-convex lens 142 of potassium chloride and a negative meniscus lens 144 of zinc selenide. The bi-convex lens 142 is aligned closest to the negative lens 106, spaced between approximately 56 and 62 and one-half mm away. There is a small air gap 146 of approximately 1 mm (0.972 mm for the preferred embodiment) between the bi-convex lens 142 and the negative meniscus lens 144.

The doublet 140 is held by a lens seating ring 152 having two flexible lens retaining tabs 150. The lens seating ring 152 is mounted onto a lens carrier shaft 154. An end of the lens carrier shaft 154 is surrounded by the lens carrier housing 114. A connector flange 156 and a clamp 158 encase the portion of the lens carrier housing 114 which surrounds the lens carrier shaft 154. This, in turn, is encased by the generally cubic portion 76 of the optical housing 52 which comprise the four counter bored holes 72 and four mounting screws 70 and couple the optical housing 52 to the mounting segment 50. Two of the mounting screws 70 are shown in FIG. 6.

The lens carrier housing 114 contains a second helical slide 160 near the second end of the lens carrier shaft 154. A second drive pin 162 is threadedly inserted into a portion of the lens carrier shaft 154 and is guided along a helical slot 164 in the second helical slide 160. The second focusing lever 90 is threadedly inserted into the second helical slide 160, its head protruding on the first side 52c of the optical housing 52 through the slot 88 which is aligned perpendicular to the optical axis 110, as shown in FIGS. 4 and 5.

None of the hardware which support optical elements ingress into the path of the optical elements. Thus, light entering the optical housing 52 through the passage 100 can travel through the optical housing 52 without significant aperture stoppage.

Referring to FIGS. 7 and 8, a schematic view of the optical system removed from the optical housing 52 of the micromanipulator 30 is shown. Due to size limitations in the drawings, the helium neon and carbon dioxide wavelengths are depicted with only a single set of light rays in FIG. 7. However, it will be understood that both of these wavelengths propagate through the optical system of FIG. 7 and both are incident on the three lenses 106, 142, and 144. In FIG. 8, a schematic, enlarged view of a portion of the first end 52a of the optical system is shown, illustrating the helium neon and carbon dioxide beams slightly separated.

The negative lens 106 is located at the second end of the optical housing, approximately 25 mm away from the nearest edge of the collet 36 (shown in FIG. 6). As described previously, the central axis of the collet 36 and the center of the negative lens 106 form an optical axis 110. Between approximately 56 mm and 62 and one-half mm away on the optical axis from the initial negative lens 106, is the doublet 140. The doublet 140 comprises the bi-convex lens 142 and the negative meniscus lens 144, with the approximately one mm air gap 146 (0.972 mm for the preferred embodiment) in between the two elements. The doublet 140 is arranged such that incident laser light contacts the bi-convex element first 142. Light transmitted through the bi-convex element 142 is incident on the approximately one millimeter wide air gap 146 (i.e., 0.972 mm for the preferred embodiment), which transmits light to the negative meniscus lens element 144. Light transmitted by the negative meniscus lens 144 is incident on the mirror 64 which is also aligned on the optical axis 110 and is mounted on the mirror arm 62 within the bell-shaped orifice 32 in the mounting segment 50.

The table below defines the micromanipulator lens specifications for the preferred embodiment of the present invention. Each of the optical elements 106, 142, and 144 have a slight protective bevel. Additionally, the zinc selenide elements 106 and 144 are coated with an antireflection coating of reflectivity equal to or less than 0.5%.

| Lens No. | Radius of Curvature | | Diameter (mm) | Center Thickness (mm) | Mat'l. |
| --- | --- | --- | --- | --- | --- |
| | $R_1$ | $R_2$ | | | |
| 106 | −9.524 | plano | 10 | 0.979 | ZnSe |
| 142 | 26.615 | −18.149 | 17.8 | 5.509 | KCl |
| 144 | −17.43 | −26.057 | 17.8 | 1.874 | ZnSe |

The index of refraction of zinc selenide ranges from approximately 2.4 to 2.6, while the index of refraction for potassium chloride ranges from 1.45 to 1.48. The average dispersions of the optical elements are as follows: 0.19 for the initial negative lens 106; 0.03 for the bi-convex lens 142; and 0.19 for the negative meniscus 144.

The potassium chloride bi-convex lens 142 is highly susceptible to damage induced by liquid, as salts are generally dissolved by liquids, including vapor or blood. However, a moisture protective coating for 10.6 microns and 0.63 microns wavelength protects the potassium chloride lens 142. Additionally, the advantageous placement of the zinc selenide negative meniscus lens 149 closer to the first end 52a of the optical housing 52 helps to protect the potassium chloride lens 142 from splashes during surgery. Thus, the potassium chloride lens 142 is well protected within the optical housing 52, ensuring that the micromanipulator 30 of the present invention provides accurate placement of the carbon dioxide cutting beam.

The micromanipulator 30 illustrated in FIGS. 1, 2, and 4 is mounted especially for use in gynecological surgery. However, the optical housing 52 can be coupled with a different mounting segment formed to fit over other surgical viewing elements, such as an operating microscope. Thus, the micromanipulator 30 of the present invention may also be used in other types of laser surgery.

The colposcope 12 (or other surgical viewing instrument) aids in the accurate placement of the carbon dioxide cutting beam by magnifying the tissue to be vaporized, allowing more accurate focusing of the helium neon aiming beam's spot, and therefore the cutting beam's spot as well.

The distance between the negative lens 106 and the spot where the two laser beams come to a focus is defined as the working distance. By changing the working distance, a surgeon can regulate the plane in which tissue is vaporized by the carbon dioxide laser beam. The working distance is modified by axially altering the position of the negative lens 106.

The size of the carbon dioxide laser spot in the plane where both the carbon dioxide and helium neon beams come to a focus is defined as the spot size. By changing the spot size, a surgeon can regulate how large an area of tissue is vaporized. The spot size is modified by axially altering the position of the doublet element 140.

The negative lens 106 is mobile via a focusing mechanism which is initiated by rotation of the knurled sleeve 92 about its cylindrical axis. The spring 134 provides tension against the drive ring 132 to yield tautness in the rotation of the knurled sleeve 92. Since the knurled sleeve 92 and the drive ring 132 are coupled via the connector 136, the knurled sleeve 92 causes the drive ring 132 to rotate. As the drive ring 132 rotates, the threadedly inserted focusing lever 128 is caused to rotate with the drive ring 132. The body of the focusing lever 138, held within the long, narrow slot 138 in the helical slide 116, causes the helical slide 116 to rotate. As the helical slide 116 rotates, the head of the drive pin 126 is guided within the helical slot 127 cut within the helical slide 116. Thus, the drive pin 126 is caused to move axially along the optical axis 110. Since the body of the drive pin 126 is threadedly inserted into the lens carrier 112, the lens carrier 112 is transported axially. The negative zinc selenide lens 106 is thereby moved axially within the optical housing 52, allowing adjustment of the working distance. This method of conversion of the rotational motion of the knurled sleeve 92 to translational motion of the negative lens 106 allows fine adjustment to be made to axial position of the lens 106 with relatively large rotational motion of the knurled sleeve 92.

The three position stops 124 on the knurled sleeve 92 are calibrated during assembly of the optical housing 52. As the drive ring 132 is moved axially against the tension of the spring 134, the body of the focusing lever 128 is moved axially within the long narrow slot 130 in the helical slide 116. When the correct spring tension is established at each position stop 124, the clamping screw 122 is tightened within the particular position stop 124. The position stops 124 cause the knurled sleeve 92 to stop rotating about the optical axis 110 until enough rotational force is applied to overcome the position stop 124. Thus, the three position stops 124 provide three predetermined working distances.

To change the spot size, the doublet 140 is mobile via a focusing mechanism comprising the second focusing lever 90. When the second focusing lever 90 is moved within the slot 88 in which it is positioned, the second helical slide is caused to rotate about the optical axis 110 along with the second focusing lever 90. The head of the second drive pin 162 is thereby guided along the helical slot 164 in the second helical slide 160. The body of the second drive pin 162 thus moves axially, causing the lens carrier shaft 154 to move axially. The motion of the lens carrier shaft 154 causes the lens carrier 152 to move axially, thereby causing the doublet 140 to be shifted axially.

The spot of the helium neon aiming beam is preferably located within the spot of the carbon dioxide cutting beam for accurate aiming of the carbon dioxide cutting beam. The micromanipulator 30 of the present invention is able to focus both beams accurately even when there are small alignment errors. The optical design of the present invention ensures that the helium neon laser spot rests within the carbon dioxide laser spot even when the beams are incident off the optical axis 110, up to at least three degrees in the same direction.

Although both focusing mechanisms alter the distance between the two lenses, it is more convenient for the surgeon to have separate adjustments for working distance and for spot size. With separate adjustments, the surgeon can determine the working distance and then adjust the spot size to vaporize a larger or smaller area in the plane determined by the working distance.

Further providing convenience for the surgeon, the optical housing 52 can be mounted such that it is accessible to both right and left handed surgeons. The optical housing 52 can be attached via the four mounting screws 70 such that the shoulder 74 is adjacent one side of the mounting segment 50, as shown in FIG. 5 for example. The optical housing 52 is then aligned at a small angle from the longitudinal axis of the mounting segment 50 and the second focusing lever 90 is easily accessible to a right handed surgeon. By rotating the optical housing 52 by 180° during assembly of the micromanipulator 30, the optical housing 52 can be aligned at a small angle on the other side of the longitudinal axis of the mounting segment 50 and the second focusing lever 90 is made easily accessible to a left handed surgeon. Thus, the spot size of the beams is ambidextrously controllable, depending upon the angular orientation of the optical housing 52 with respect to the mounting segment 50.

The surface curvatures of the two lenses 142 and 144 of the doublet 140 are adjusted by computer optimization to produce an output beam in which aberrations are well corrected and the system is limited only by diffraction. The air space 146 between the two lenses 142 and 144 is helpful in correcting some aberrations, but is not entirely necessary. The adjacent surfaces of the potassium chloride bi-convex lens 142 and the zinc selenide negative meniscus 144 lens can be matched and placed in contact with a small loss of beam quality at the helium neon wavelength.

One skilled in the art will realize that the micromanipulator 30 can be mounted on any surgical viewing apparatus by changing the shape of the orifice in the mounting segment 50 to fit over the surgical viewing apparatus. Additionally, one skilled in the art will realize that any type of focusing mechanism can be employed by the micromanipulator 30 so long as it will change the distance between the negative lens 106 and the doublet 140 to enable accurate placement and sizing of the laser spot.

Although the preferred embodiment of the achromat has been discussed in reference to an aiming beam comprising helium-neon light having a wavelength of 633 nanometers, this preferred embodiment will also work with wavelengths close to 633 nanometers, such as that produced by a laser diode emitting visible light having a wavelength of 670 nanometers. Additionally, modifications of the above described embodiment can be readily made by those skilled in the art to adapt the optical elements for any of a variety of visible wavelengths.

What is claimed:

1. An apparatus for delivery of laser energy for a laser surgery system, comprising:
   an articulated arm comprising a wavelength for propagating laser light and at least one knuckle joint, said knuckle joint having a dichroic mirror to change the direction of said propagating laser light by reflecting substantially all of said laser light, said knuckle joint disposed proximate to a distal end of said articulated arm; and
   a visible light source to provide an aiming beam, said visible light source positioned to introduce said visible light into said waveguide through said dichroic mirror at said knuckle joint.

2. The apparatus of claim 1, wherein said visible light source is a laser diode.

3. The apparatus of claim 2, wherein said aiming beam has a wavelength of about 670 nanometers.

4. The apparatus of claim 2, wherein said laser diode is positioned such that said visible light propagates substantially parallel to said waveguide prior to said visible light being introduced into said waveguide.

5. The apparatus of claim 1, wherein said visible light source is a helium neon laser.

6. The apparatus of claim 1, wherein said laser light is produced by a carbon dioxide laser.

7. The apparatus of claim 1, additionally comprising a mirror to reflect said visible light onto said dichroic mirror.

8. The apparatus of claim 1, wherein said visible light is introduced into said waveguide such that an axis of propagation of said aiming beam is aligned with an axis of propagation of said laser light.

9. The apparatus of claim 1, additionally comprising a collimating lens.

10. The apparatus of claim 1, additionally comprising a focusing lens.

11. An apparatus for delivery of laser energy for a laser surgery system, comprising:
    a laser source for emitting invisible light having a first wavelength;
    a waveguide linkage for directing said invisible light along an axis of propagation, said linkage formed by a plurality of coupled waveguide segments;
    a laser diode for emitting visible light having a second wavelength; and
    a dichroic mirror in said waveguide linkage for reflecting light of one of said wavelengths while transmitting light of another of said wavelengths, said diode disposed proximate to a distal end of said waveguide linkage and positioned such that said visible light is received by said dichroic mirror to combine the visible and invisible light for propagation along said axis of propagation.

12. The apparatus of claim 11, additionally comprising at least one knuckle joint, wherein said dichroic mirror is disposed at said knuckle joint.

13. The apparatus of the claim 11, additionally comprising plural lenses mounted to receive light from said waveguide linkage, one of said lenses consisting of potassium chloride and another of said lenses consisting of zinc selenide.

* * * * *

UNITED STATES PATENT AND TRADEMARK OFFICE
CERTIFICATE OF CORRECTION

PATENT NO. : 5,289,557
DATED : February 22, 1994
INVENTOR(S) : Andrew I. Sheinis et al It is certified that error appears in the above-indentified patent and that said Letters Patent is hereby corrected as shown below:

Column 11, claim 1, line 3, change "wavelength" to --waveguide --.

Signed and Sealed this

Sixth Day of September, 1994

Attest:

BRUCE LEHMAN

*Attesting Officer*              *Commissioner of Patents and Trademarks*